United States Patent [19]

Snell et al.

[11] 3,962,442

[45] June 8, 1976

[54] FUNGICIDAL COMPOSITIONS CONTAINING 2-AMINO PYRIMIDINES AND METHODS OF USING THE SAME

[75] Inventors: Brian Kenneth Snell; Ranaji Ghosh, both of Bracknell, England

[73] Assignee: Imperial Chemical Industries Limited, London, England

[22] Filed: Jan. 26, 1971

[21] Appl. No.: 109,931

Related U.S. Application Data

[62] Division of Ser. No. 623,810, March 17, 1967, abandoned.

[52] U.S. Cl. ............................... 424/251; 424/248; 424/267
[51] Int. Cl.² ..................... A01N 9/00; A01N 9/22; A01N 9/28
[58] Field of Search ..................... 424/251, 248, 267

[56] References Cited

UNITED STATES PATENTS

| 3,092,545 | 6/1963 | Williamson | 424/251 |
|---|---|---|---|
| 3,227,612 | 1/1966 | Gershon | 424/251 |
| 3,287,453 | 11/1966 | McHattie | 260/256.4 |

*Primary Examiner*—Sam Rosen
*Assistant Examiner*—Daren M. Stephens
*Attorney, Agent, or Firm*—Cushman, Darby & Cushman

[57] ABSTRACT

Fungicidally effective 2-amino pyrimidines bearing in the 6-position a carboxyl- or sulphonyl-esterified hydroxy or mercapto group; or salts thereof.

10 Claims, No Drawings

FUNGICIDAL COMPOSITIONS CONTAINING 2-AMINO PYRIMIDINES AND METHODS OF USING THE SAME

This is a division of our copending application Ser. No. 623,810, filed Mar. 17, 1967, and now abandoned.

This invention relates to new pyrimidine derivatives, to processes for making them, to biologically active compositions containing them and to methods for combating pests.

Accordingly this invention provides, as new compounds, 2-amino pyrimidines bearing in the 6-position a carboxyl or sulphonyl-esterified hydroxy or mercapto group; or salts thereof.

More particularly the invention provides a pyrimidine derivative having the formula:

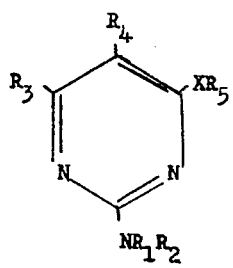

or a salt thereof, wherein $R_1$ and $R_2$ represent atoms of hydrogen, substituted or unsubstituted hydrocarbon groups, or together with the adjacent N-atom form a heterocyclic ring which may contain one or more additional hetero- atoms; $R_3$ and $R_4$ represent atoms of hydrogen or halogen, substituted or unsubstituted hydrocarbon groups, or nitro groups; X represents an atom of oxygen or sulphur; and $R_5$ is a carbonyl or sulphonyl group bearing directly, or through an oxygen or sulphur atom, a substituted or unsubstituted hydrocarbon group, or a heterocyclic group.

More specifically, the invention provides a pyrimidine derivative having the formula:

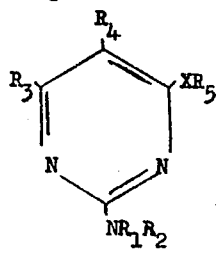

or a salt thereof, wherein $R_1$ and $R_2$ represent hydrogen atoms, lower alkyl radicals, a halophenyl radical, a piperidino radical, a morpholino radical, or a 1-methyl-piperazin-4-yl radical; $R_3$ represents a hydrogen atom, a lower alkyl radical or a phenyl radical; $R_4$ represents an atom of hydrogen or bromine, a lower alkyl, lower alkenyl, or benzyl radical, or a nitro group; X represents an atom of oxygen or sulphur; and $R_5$ is a carbonyl or sulphonyl group bearing directly, or through an atom of oxygen or sulphur, a lower alkyl radical, a lower alkenyl radical, a phenyl radical or a nitro-, halo-, lower alkyl- substituted phenyl radical, a piperidino radical, a furyl radical or a styryl radical.

Preferred pyrimidine derivatives according to this invention are those having the general formula set out above wherein $R_1$ and $R_2$ represent hydrogen, or lower alkyl radicals; $R_3$ represents hydrogen, a lower alkyl radical or a phenyl radical; $R_4$ represents an atom of bromine, a lower alkyl, lower alkenyl or benzyl radical, and $R_5$ is a carbonyl or sulphonyl group bearing a lower alkyl radical, a lower alkoxy radical, a lower alkylthio radical, a phenyl radical or a nitro-, lower alkyl- or halo-substituted phenyl radical, a phenylthio radical, an alkenyl radical, an aralkenyl radical or a piperidine or furyl radical; or a salt thereof.

Particular biologically active pyrimidine derivatives according to the invention are those wherein $R_1$ and $R_2$ are hydrogen or lower alkyl radicals; $R_3$ is a lower alkyl radical; $R_4$ is a lower alkyl radical having 2 to 6 carbon atoms; and $R_5$ is a carbonyl or sulphonyl group bearing a lower alkyl radical, a lower alkoxy radical, a phenyl radical or a styryl radical.

Preferred particularly biologically active pyrimidine derivatives are those wherein $R_1$ and $R_2$ are both methyl radicals or $R_1$ is hydrogen and $R_2$ is an ethyl radical; $R_3$ is a methyl radical; $R_4$ is a butyl or amyl radical; X is an atom of oxygen; and $R_5$ is lower alkyl, lower alkoxy or phenyl radical.

Specific pyrimidine derivatives of the invention which have been found to be particularly useful are listed in the Table I below. The headings to the columns of the Table correspond to the substituent groups on the pyrimidine ring in the general formula set out above.

TABLE I

| COMPOUND NO. | $NR_1R_2$ | $R_3$ | $R_4$ | $XR_5$ |
|---|---|---|---|---|
| 1 | $-N(CH_3)_2$ | $CH_3$ | $nC_3H_7$ | $O-CO-C_6H_4-NO_2$ |
| 2 | $-N(CH_3)_2$ | $CH_3$ | $nC_3H_7$ | $O-CO-C_6H_5$ |
| 3 | $-N(CH_3)_2$ | $CH_3$ | $nC_3H_7$ | $O-SO_2C_6H_5$ |
| 4 | $-N(CH_3)_2$ | $CH_3$ | $-CH_2-CH=CH_2$ | $O-CO-C_6H_4NO_2(p)$ |
| 5 | $-N(CH_3)_2$ | $CH_3$ | $nC_3H_7$ | $O-SO_2-C_6H_4-CH_3(p)$ |
| 6 | $-N(CH_3)_2$ | $CH_3$ | $nC_3H_7$ | $O-SO_2-CH_3$ |
| 7 | $-N(CH_3)_2$ | $CH_3$ | $nC_3H_7$ | $O-C(=O)-S-C_6H_5$ |
| 8 | $-N(CH_3)_2$ | $CH_3$ | $nC_5H_{11}$ | $O-CO-C_6H_5$ |
| 9 | $-N(CH_3)_2$ | $CH_3$ | $nC_3H_7$ | $-O-CO-C_6H_4-Cl(m)$ |
| 10 | $-N(CH_3)_2$ | $CH_3$ | $nC_4H_9$ | $O-CO-C_6H_5$ |
| 11 | $-N\smile N-CH_3$ | $CH_3$ | $nC_4H_9$ | $O-SO_2-CH_3$ |
| 12 | $-N(CH_3)_2$ | $CH_3$ | $nC_5H_{11}$ | $O-SO_2-CH_3$ |
| 13 | $-N(CH_3)_2$ | $CH_3$ | $nC_4H_9$ | $O-SO_2-CH_3$ |

TABLE I-continued

| COMPOUND NO. | NR₁R₂ | R₃ | R₄ | XR₅ |
|---|---|---|---|---|
| 14 | —N(CH₃)₂ | CH₃ | nC₃H₇ | O—CO—CH₃ |
| 15 | —N(CH₃)₂ | CH₃ | nC₃H₇ | O—SO₂—C₆H₄—NO₂(m) |
| 16 | —N(CH₃)₂ | CH₃ | nC₃H₇ | O—CO-(tetrahydrofuryl) |
| 17 | —N(CH₃)₂ | CH₃ | H | O—SO₂—CH₃ |
| 18 | —N(CH₃)₂ | CH₃ | nC₄H₉ | S—CO—OC₂H₅ |
| 19 | —N(morpholino) | CH₃ | H | O—SO₂CH₃ |
| 20 | —N(morpholino) | C₆H₅ | H | O—SO₂CH₃ |
| 21 | —N(morpholino) | CH₃ | H | O—SO₂—C₂H₅ |
| 22 | —N(CH₃)₂ | CH₃ | C₂H₅ | O-CO-C₆H₅ |
| 23 | —N(morpholino) | CH₃ | H | O-SO₂-C₆H₄-CH₃ |
| 24 | —N(morpholino) | CH₃ | H | O-SO₂-C₆H₅ |
| 25 | —N(CH₃)₂ | CH₃ | SecC₃H₇ | O-CO-C₆H₅ |
| 26 | —N(CH₃)₂ | CH₃ | nC₃H₇ | O—CO—CH=CH—CH₃ |
| 27 | —N(CH₃)₂ | CH₃ | nC₃H₇ | O-CO-CH=CH-C₆H₅ |
| 28 | —NH—C₂H₅ | CH₃ | nC₄H₉ | O-CO-C₆H₅ |
| 29 | —N(piperidino) | CH₃ | H | O-CO-C₆H₅ |
| 30 | —N(CH₃)₂ | H | H | O—SO₂—CH₃ |
| 31 | —N(CH₃)₂ | CH₃ | Br | O-CO-C₆H₅ |
| 32 | | CH₃ | H | -NH-C₆H₄-Cl |
| 33 | —N(CH₃)₂ | CH₃ | nC₄H₉ | O-CO-C₆H₅ |
| 34 | —N(CH₃)₂ | CH₃ | CH₃ | O—CO—OC₂H₅ |
| 35 | —N(CH₃)₂ | CH₃ | CH₃ | O—CO—OnC₄H₉ |
| 36 | —N(CH₃)₂ | CH₃ | CH₃ | S—CO—OnC₃H₇ |
| 37 | —N(CH₃)₂ | CH₃ | nC₃H₇ | S—CO—OnC₃H₇ |
| 38 | —N(CH₃)₂ | CH₃ | nC₄H₉ | O—CO—OC₂H₅ |
| 39 | —N(CH₃)₂ | CH₃ | nC₄H₉ | O—CO—OnC₃H₇ |
| 40 | —N(CH₃)₂ | CH₃ | nC₄H₉ | O—CO—OnC₄H₉ |
| 41 | —N(CH₃)₂ | CH₃ | nC₄H₉ | S—CO—OnC₃H₇ |
| 42 | —N(morpholino) | nC₃H₇ | H | S-CO-C₆H₅ |
| 43 | —N(CH₃)₂ | nC₃H₇ | C₂H₅ | O-CO-C₆H₅ |
| 44 | —N(CH₃)(C₂H₅) | CH₃ | nC₄H₉ | O-CO-C₆H₅ |
| 45 | —NH₂ | C₆H₅ | H | O-CO-C₆H₅ |
| 46 | —N(CH₃)₂ | CH₃ | | O-CO-C₆H₅ |

TABLE I-continued

| COMPOUND NO. | NR₁R₂ | R₃ | R₄ | XR₅ |
|---|---|---|---|---|
| 47 | —N(CH₃)₂ | CH₃ | H | O-SO₂-N⟨  ⟩  |
| 48 | —N(CH₃)₂ | H | NO₂ | O-CO-⟨  ⟩  |

Compound No. 14 in Table I above is readily hydrolysed by water.

In this specification the numbering of the pyrimidine ring is as follows:

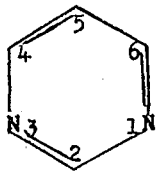

It may be noted that the 4- and 6- positions are equivalent.

As suitable salts of the pyrimidine derivatives of this invention there may be mentioned, for example, the hydrochlorides.

According to a further feature of the invention, we provide the novel pyrimidine derivatives listed in Table I herein above.

The invention also provides a process for making the pyrimidine derivatives of this invention which comprises reacting a compound of the formula:

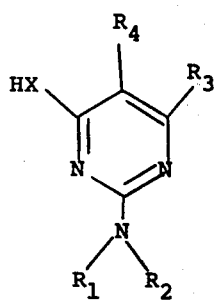

wherein $R_1$, $R_2$, $R_3$, $R_4$ and X have any of the meanings stated above with an acyl or sulphonyl halide of the formula:

$$R_5 — Hal$$

wherein $R_5$ has any of the meanings stated above and Hal represents a halogen atom, under conditions where the hydrogen halide which is formed is removed as it is produced.

The foregoing process is preferably carried out in the presence of a diluent as a reaction medium and suitable diluents include substances acting as solvents for either or both of the reactants. Suitable solvents are organic solvents, for example benzene, toluene, lower aliphatic ketones such as methyl ethyl ketone or acetonitrile. A particularly preferred solvent is ethyl acetate.

The hydrogen halide produced during the reaction may be removed, for example, by carrying out the reaction in the presence of an acid acceptor. Suitable acid acceptors are bases or a salt of a strong base and a weak acid. If a base is used it may be, for example, a tertiary amine. Preferred tertiary amines are triethylamine and pyridine. The base may also be, for example, and alkali or alkaline earth metal hydroxide, for example, sodium hydroxide. If a salt of a strong base and a weak acid is used as the acid acceptor then a suitable salt is an alkali or alkaline earth metal carbonate. A preferred such salt is potassium carbonate.

The invention further provides a process for making the pyrimidine derivatives of the invention which comprises reacting the appropriate acyl or sulphonyl halide with a metallic salt of the appropriate 6-hydroxy- or 6-mercapto- pyrimidine, if necessary in the presence of a solvent to facilitate the reaction. Suitable solvents include those recited above.

The pyrimidine derivatives of the invention possess activity against a wide variety of fungal diseases including the following specific diseases:
  Puccinia recondita (rust) on wheat
  Phytophthora infestans (late blight) on tomatoes
  Sphaerotheca fuliginea (powdery mildew) on cucumber
  Erysiphe graminis (powdery mildew) on wheat and barley
  Podosphaera leucotricha (powdery mildew) on apple
  Uncinula necator (powdery mildew) on vine
  Plasmopara viticola (downy mildew) on vine
  Piricularia oryzae (blast) on rice
  Venturia inaequalis (scab) on apple
  Pythium ultimum (seedling rot) on peas
  Fusarium culmorum (stem rot) on wheat The compounds of the present invention are toxic towards a variety of insect pests including mosquito larvae (Aedes aegypti), black aphids (Aphis fabae), green aphids (Macrosiphum pisi), red spider mites (Tetranychus telarius), mustard beetles (Phaedon cochleariae), and root knot nematodes (Meloidogyne incognita).

A particularly useful feature of the activity of the pyrimidine derivatives of the invention is their systemic effect, that is to say, their ability to move throughout the plant to reach any part thereof bearing a fungal infection and/or insect infestation and to combat the same.

We have found that the biological activity of the novel pyrimidine derivatives of the invention is decreased if both $R_3$ and $R_4$ are hydrogen, or if $R_4$ is an alkyl radical containing more than 7 carbon atoms.

A particularly useful pyrimidine derivative is that in which $R_1$ and $R_2$ are both methyl, $R_3$ is methyl, $R_4$ is $nC_4H_9$, and $XR_5$ is $O-CO-C_6H_5$, that is Compound No. 10 in the foregoing Table I.

According to a preferred embodiment of the invention, we accordingly provide fungicidal compositions comprising as active ingredient 2-dimethylamino-4-methyl-5-n-butyl-6-phenylcarbonyloxy-pyrimidine.

Other particularly useful pyrimidine derivatives are the compounds numbered 8, 10, 12, 13, 27, 28, 39, 40 and 41 in Table I above.

The biologically active pyrimidine derivatives of this invention are used to combat plant pests in a number of ways. Thus they can be applied to the foliage of an infected plant, to seed or to the soil in which plants are growing or to be planted.

In a further aspect, therefore, the invention includes a method for the combating of undesired fungal infections in plants which comprises applying to the locus of the plant a pyrimidine derivative as hereinbefore defined or a composition as hereinafter defined.

In a yet further aspect the invention includes a method of combating insect infestations in plants which comprises applying to the locus of the plant an insecticidically active pyrimidine derivative as hereinbefore defined or a composition as hereinafter defined.

In yet a further aspect the invention includes a method for treating agricultural soil comprising applying to the soil a pyrimidine derivative as hereinbefore defined or a composition as hereinafter defined.

The invention includes, therefore, a method of combating plant pathogens which comprises applying to a plant, or to seed thereof, a pyrimidine derivative as hereinbefore defined or a composition as hereinafter defined.

The pyrimidine derivatives of this invention are preferably used in the form of compositions and these compositions may be used for agricultural and horticultural purposes. The type of composition used in any instance will depend upon the particular purpose for which it is to be used.

The compositions may be in the form of dusting powders or granules wherein the active ingredient is mixed with a solid diluent or carrier. Suitable solid diluents or carriers may be, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent assisting the adhesion of the composition to the seed, for example a mineral oil. The compositions may also be in the form of dispersible powders or grains comprising, in addition to the active ingredient, a wetting agent to facilitate the dispersion of the powder or grains in liquids. Such powders or grains may include fillers, suspending agents and the like.

The compositions may also be in the form of liquid preparations to be used as dips or sprays which are generally aqueous dispersions or emulsions containing the active ingredient in the presence of one or more wetting agents, dispersing agents, emulsifying agents or suspending agents.

Wetting agents, dispersing agents and emulsifying agents may be of the cationic, anionic or non-ionic type. Suitable agents of the cationic type include, for example, quaternary ammonium compounds, for example, cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butyl-naphthalene sulphonate, and a mixture of the sodium salts of diisopropyl- and triisopropyl-naphthalene sulphonic acids. Suitable agents of the non-ionic type include, for example, the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins.

Suitable suspending agents are, for example, hydrophilic colloids, for example polyvinylpyrrolidone and sodium carboxymethylcellulose, and the vegetable gums, for example gum acacia and gum tragacanth.

The aqueous dispersions or emulsions may be prepared by dissolving the active ingredient or ingredients in an organic solvent which may contain one or more wetting, dispersing or emulsifying agents and then adding the mixture so obtained to water which may likewise contain one or more wetting, dispersing or emulsifying agents. Suitable organic solvents are ethylene dichloride, isopropyl alcohol, propylene glycol, diacetone alcohol, toluene, kerosene, methylnaphthalene, xylenes and trichloroethylene.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example for improving the distribution, adhesive power and resistance to rain on treated surfaces, the different compositions can be better adapted for the various uses for which they are intended.

The pyrimidine derivatives may also be conveniently formulated by admixing them with fertilizers. A preferred composition of this type comprises granules of fertiliser material incorporating, for example coated with, a pyrimidine derivative. The fertiliser material may, for example, comprise nitrogen or phosphate-containing substances.

In yet a further aspect of the invention, therefore, we provide a fertiliser composition comprising a pyrimidine derivative as hereinbefore defined.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may conveniently contain from 10–85% by weight of the active ingredient or ingredients and generally from 25–60% by weight of the active ingredient or ingredients. When diluted to form aqueous preparations, such preparations may contain varying amounts of the active ingredient or ingredients depending upon the purpose for which they are to be used, but an aqueous preparation containing between 0.001% and 1.0% by weight of active ingredient or ingredients may be used.

It is to be understood that the biologically active compositions of this invention may comprise, in addition to a pyrimidine derivative, one or more other compounds having biological activity. They may also incorporate one or more stabilizing agents, for example epoxides, for example epichlorhydrin.

The invention is illustrated by the following Examples, those numbered 1 to 5 exemplifying methods of preparing the pyrimidine compounds listed in Table I above, while those numbered 6 to 13 are illustrative of compositions containing various of the pyrimidine derivatives as active ingredient. In the latter group all references to percentage amounts of constituents are by weight and are based on the weight of the compositions as a whole.

EXAMPLE 1

2-Dimethylamino-4-methyl-6-(4'-nitrophenyl)carbonyloxy-5-n-propylprimidine, (Compound No. 1, Table I) having the formula:

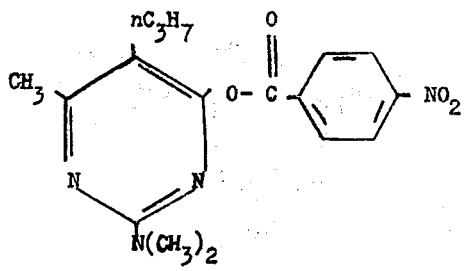

was prepared as follows: 2-dimetylamino-4-methyl-6-hydroxy-5-n-propylpyrimidine (1.95 g., 0.01 mole) was added to a solution of sodium (0.23 g., 0.01 mole) in dry ethanol (25 ml.). The solution was kept at 40°C for 1 hour, the solvent removed in vacuo, and the residue dried by azeotropic distillation with benzene. To the residue was added dry benzene (25 ml.) and freshly prepared p-nitrobenzoyl chloride (2.3 g., 0.012 mole) and the reaction mixture stirred and refluxed for 4 hours. The cooled mixture was shaken with ice-cold 5% aqueous sodium hydroxide solution, washed with water until the washings were neutral, and the benzene layer dried (Na₂SO₄). Removal of the benzene, followed by removal of last traces of solvent at the oil pump, gave a viscous residue which crystallised on trituration with petroleum ether. Recrystallisation from ethanol gave a product, m.p. 109°C. (1.8 g., 53%).

Although the above reaction was conducted in benzene, other solvents such as toluene, lower aliphatic ketones such as methyl ethyl ketone, acetonitrile and ethyl acetate were found to be suitable for the purpose. The preferred solvent is ethyl acetate.

The following compounds were also prepared by the method of Example 1.

| Compound No. | Physical Characteristic | Solvent of Crystallisation |
| --- | --- | --- |
| 2 | m.p. 58° | EtOH |
| 3 | m.p. 72° | EtOH |
| 4 | m.p. 114° | EtOH |
| 5 | m.p. 68° | EtOH |
| 6 | m.p. 71° | EtOH |
| 7 | b.p. 150–155°/0.1 mm. | — |
| 8 | m.p. 57° | EtOH |
| 9 | m.p. 89° | EtOH |
| 10 | m.p. 59° | EtOH |
| 11 | m.p. 162° | EtOH |
| 13 | m.p. 67° | EtOH |
| 14 | m.p. 69° | EtOH |
| 15 | m.p. 109° | EtOH |
| 16 | m.p. 71° | EtOH |
| 17 | m.p. 87° | EtOH |
| 22 | m.p. 89° | EtOH |
| 23 | m.p. 104–105° | MeOH |
| 25 | m.p. 63° | EtOH |
| 26 | $n_D^{21} = 1.5282$ | — |
| 27 | m.p. 88° | EtOH |
| 28 | m.p. 69–70° | EtOH/H₂O |
| 29 | m.p. 120° | EtOH |
| 30 | m.p. 76° | EtOH |
| 31 | m.p. 128–129° | EtOH |
| 32 | m.p. 114–116° | EtOH |
| 42 | m.p. 40–46° | EtOH |
| 43 | m.p. 62° | EtOH |
| 44 | m.p. 45° | iso-propyl-alcohol |
| 45 | m.p. 122–123° | iso-propyl-alcohol |
| 46 | m.p. 92° | EtOH |
| 47 | $n_D^{20} = 1.5251$ | — |
| 48 | m.p. 125–126° | EtOH |

EXAMPLE 2

S-(5-n-Butyl-2-dimethylamino-4-methyl-6-pyrimidyl) O-ethylthiolcarbonate (Compound No. 18, Table I) having the formula:

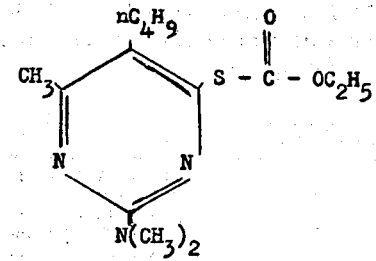

was prepared as follows:- 5-n-Butyl-2-dimethylamino-4-methyl-6-mercapto-pyrimidine (6.75 g.) was dissolved in a solution of sodium hydroxide (1.3 g.) in water (100 ml.). Ethyl chloroformate (3.3 g.) was added and the reaction mixture stirred at room temperature for 3 hours. The product was obtained by extraction with ether. The ether extracts were washed with water, dried (Na₂SO₄), and the solvent removed to leave a viscous oil, $n_D^{26} = 1.5444$.

The following compound was also prepared by the method of Example 2.

| Compound No. | Physical Characteristics |
| --- | --- |
| 33 | b.p. 174–177°/0·12 mm. $n_D^{20} = 1·6008$ |

EXAMPLE 3

This Example illustrates the preparation of 5-n-butyl-2-dimethylamino-4-ethoxy-carbonyloxy-6-methylpyrimidine (Compound No. 38, Table I) having the structure:

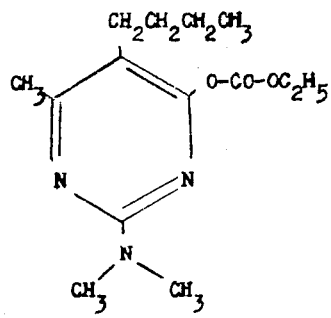

To a solution of 5-n-butyl-2-dimethylamino-4-hydroxy-6-methyl pyrimidine (5.0 g.) in pyridine (100 c.c.) ethylchloroformate (2.9 g.) was added dropwise, and the mixture stirred and kept at ambient temperature for 72 hours. The pyridine was removed from the mixture by evaporation at reduced pressure, and the residual mixture distributed between water and methylene chloride. The aqueous layer was discarded and the methylene chloride solution washed twice with water, then twice with an equal volume of a 4% solution of sodium hydroxide, and finally with water until the washings were neutral. After drying the methylene chloride solution over anhydrous sodium sulphate, and filtering to remove the solid, the methylene chloride was evaporated off and the residual oil distilled. 5-n-butyl-2-dimethylamino-4-ethoxy-carbonyloxy-6-methylpyrimidine was obtained as a colourless oil, b.p. 109°–110° at 0.01 mm. Hg, $n_D^{22.5}$ = 1.5034.

The following compounds were also obtained by the method of Example 3.

| Compound No. | b.p. |
|---|---|
| 34 | 106–109°C/0.01 mm. |
| 35 | 105°C/0.03 mm. |
| 36 | 119–120°C/0.05 mm. |
| 37 | 99–101°C/0.02 mm. |
| 39 | 118–119°C/0.04 mm. |
| 40 | 122–123°C/0.01 mm. |
| 41 | 132–134°C/0.015 mm. |

EXAMPLE 4

4-Methyl-6-methylsulphonyloxy-2-morpholinopyrimidine, (Compound No. 19, Table I) having the formula:

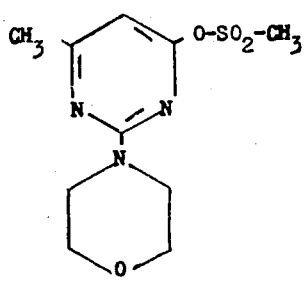

was prepared as follows: 4-hydroxy-6-methyl-2-morpholinopyrimidine (4.87 g., 0.025 mole) was suspended in dry dimethylformamide (25 ml.) and to the stirred suspension was added, all at once, 2 ml., 0.025 mole of methane sulphonyl chloride. To the stirred mixture was added, dropwise from a burette, 3.5 ml., 0.025 mole of triethylamine. The temperature of the reaction mixture rose to 42°C., and the mixture became almost clear. Stirring was continued for 2 hours, the solution filtered, and the filtrate was poured into ice-water. The precipitated material was filtered off, washed with a little ice-cold water, and dried. Recrystallisation from ethanol gave the product, 4.05 g. (68%) m.p. 131°C.

The following compounds were also prepared by the method of Example 4.

| Compound No. | Physical Characteristic | Solvent of Crystallisation |
|---|---|---|
| 20 | m.p. 138°C. | EtOH |
| 21 | m.p. 76°C. | EtOH |
| 24 | m.p. 113–114°C. | EtOH |

EXAMPLE 5

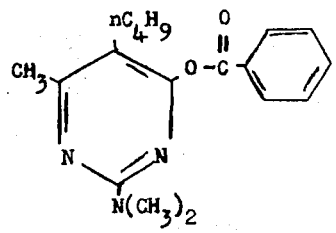

5-n-Butyl-2-dimethylamino-4-methyl-6-phenylcarbonyloxypyrimidine, (Compound No. 10, Table I) having the above formula, was prepared as follows:- a mixture of 5-n-butyl-2-dimethylamino-4-hydroxy-6-methylpyrimidine (4.18 g., 0.02 mole), anhydrous potassium carbonate (2.76 g., 0.02 mole), benzoyl chloride (2.81 g., 0.02 mole) and ethyl acetate (50 ml.) was stirred and heated under reflux for 7 hours. The reaction mixture was left at room temperature overnight, the solvent removed in vacuo, and the residue taken up in toluene (100 ml.). The toluene was washed with ice-cold 5% aqueous sodium hydroxide solution, then with water until the washings were neutral, and finally dried (MgSO$_4$). Removal of the toluene in vacuo left the product as a white crystalline solid (5.2 g., 83%) which was recrystallised from ethanol, m.p. 59°C.

The above reaction was found to proceed satisfactorily in the solvents benzene, toluene, methyl ethyl ketone and acetonitrile. Ethyl acetate was also a suitable solvent.

In the following Examples the words: LUBROL, AROMASOL, DISPERSOL, LISSAPOL, CELLOFAS are Trade Marks.

EXAMPLE 6

An emulsion concentrate was made up by mixing together the ingredients set out below in the proportions stated and stirring the mixture until all the constituents were dissolved

| | |
|---|---|
| Compound No. 10 | 10% |
| Ethylene Dichloride | 40% |

| | |
|---|---|
| Calciumdodecylbenzene- sulphonate | 5% |
| "Lubrol" L | 10% |
| "Aromasol" H | 35% |

EXAMPLE 7

A composition in the form of grains readily dispersible in a liquid, e.g. water, was prepared by grinding together the first three of the ingredients listed below in the presence of added water and then mixing in the sodium acetate. The resultant mixture was dried and passed through a British Standard mesh sieve, size 44-100, to obtain the desired size of grains.

| | |
|---|---|
| Compound No. 10 | 50% |
| "Dispersol" T | 25% |
| "Lubrol" APN5 | 1.5% |
| Sodium acetate | 23.5% |

EXAMPLE 8

The ingredients listed below were all ground together in the proportions stated to produce a powder formulation readily dispersible in liquids.

| | |
|---|---|
| Compound No. 10 | 45% |
| "Dispersol" T | 5% |
| "Lissapol" NX | 0.5% |
| "Cellofas" B600 | 2% |
| Sodium acetate | 47.5% |

EXAMPLE 9

The active ingredient (Compound No. 10 of Table I) was dissolved in a solvent and the resultant liquid was sprayed onto the granules of Fuller's earth. The solvent was then allowed to evaporate to produce a granular composition.

| | |
|---|---|
| Compound No. 10 | 5% |
| Fuller's earth or China clay granules | 95% |

EXAMPLE 10

A composition suitable for use as a seed dressing was prepared by mixing all three of the substituents set out below in the proportions stated.

| | |
|---|---|
| Compound No. 10 | 50% |
| Mineral oil | 2% |
| China clay | 48% |

EXAMPLE 11

A dusting powder was prepared by mixing, in the proportions stated, the active ingredient with talc.

| | |
|---|---|
| Compound No. 10 | 5% |
| Talc | 95% |

EXAMPLE 12

A Col formulation was prepared by ball-milling the constituents set out below and then forming an aqueous suspension of the ground mixture with water.

| | |
|---|---|
| Compound No. 10 | 40% |
| "Dispersol" | 10% |
| "Lubrol" | 1% |
| Water | 49% |

EXAMPLE 13

Formulations similar to those set out in Examples 6–12 above but containing as active ingredient a compound numbered 5, 6, 8, 9, 11 to 13, 27, 28, 35 to 41 respectively, from Table I above, were prepared by methods similar to those described in each particular Example.

Compositions according to the invention were made up in the following manner and tested against various fungal diseases, and the results of these tests are shown in Tables II and III hereinafter. In the tests, both a protected and an eradicant test were carried out, and in the protectant test the plants were sprayed so that the leaves were wetted with a solution or suspension containing 500 parts per million of the active compound and 0.1% of a wetting agent, and after 24 hours were inoculated with the disease, the extent of which was assessed visually at the end of the test. In the eradicant test, the plants were inoculated with the disease and then sprayed (so that the leaves were wetted) after a number of days depending on the disease with a solution or suspension containing 500 parts per million of the active compound and 0.1% of a wetting agent. The results are shown in Table II below as a grading giving the percentage amount of disease as follows:

| Grading | Percentage Amount of Disease |
|---|---|
| 0 | 61 to 100 |
| 1 | 26 to 60 |
| 2 | 6 to 25 |
| 3 | 0 to 5 |

TABLE II

| Compound No. | PUCCINIA RECONDITA (Rust) Wheat 10 | | PHYTOPHTHORA INFESTANS (Late Blight) Tomato 4 | | SPHAEROTHECA FULIGINEA (Powdery Mildew) Cucumber 10 | | ERYSIPHE GRAMINIS (Powdery Mildew) Wheat 10 | | ERYSIPHE GRAMINIS (Powdery Mildew) Barley 10 | | PODOSPHAERA LEUCOTRICHA (Powdery Mildew) Apple 7–14 | | UNCINULA NECATOR (Powdery Mildew) Vine 14 | | PLASMOPARA VITICOLA (Downy Mildew) Vine 7 | | PIRICULARIA ORYZAE (Blast) Rice 7 | | VENTURIA INAEQUALIS (Scab) Apple 14 | |
|---|---|---|---|---|---|---|---|---|---|---|---|---|---|---|---|---|---|---|---|---|
| | Prot | Erad | Prot | Erad | Prot | Erad | Prot | Erad | Prot | Erad | Prot | Erad | Prot | Erad | Prot | Erad | Prot | Erad | Prot | Erad |
| 1 | 0 | 0 | 0 | — | 3 | — | — | — | G1— | — | — | — | — | — | — | — | — | — | — | — |
| 2 | 0 | 0 | 0 | — | 3 | 3 | 3 | — | 3 | — | 3 | 3 | 1 | — | 2 | — | — | — | 0 | — |
| 3 | 0 | 0 | 0 | — | 3 | 1 | — | — | — | — | — | — | — | — | — | — | — | — | — | — |
| 4 | 0 | 0 | 1 | — | 3 | 3 | 2 | — | 2 | — | 1 | — | 0 | — | 0 | — | — | — | 0 | — |
| 5 | 0 | 0 | 2 | — | 3 | 2 | — | — | — | — | — | — | — | — | — | — | — | — | — | — |
| 6 | 0 | 0 | 3 | — | 3 | 2 | — | — | — | — | — | — | — | — | — | — | — | — | — | — |
| 7 | 0 | 0 | 2 | — | 3 | 3 | — | — | — | — | — | — | — | — | — | — | — | — | — | — |
| 8 | 1 | 0 | 2 | — | 3 | 3 | 3 | — | 3 | — | 3 | 3 | 3 | — | 0 | — | 3 | — | 0 | — |
| 9 | 1 | 0 | 2 | — | 3 | 3 | 3 | — | 3 | — | 3 | — | 1 | — | 1 | — | 3 | — | 0 | — |
| 10 | 2 | 0 | 2 | — | 3 | 3 | 3 | — | 3 | — | 3 | — | 3 | — | 1 | — | 1 | — | 0 | — |
| 11 | 0 | 0 | 2 | — | 2 | 2 | — | — | — | — | — | — | — | — | — | — | — | — | — | — |
| 12 | 1 | 0 | 3 | — | 3 | 3 | — | — | — | — | — | — | — | — | — | — | — | — | — | — |
| 13 | 0 | 0 | 3 | — | 3 | 3 | — | — | — | — | — | — | — | — | — | — | — | — | 13 | — |
| 14 | — | — | — | — | 3 | 3 | — | — | — | — | — | — | — | — | — | — | — | — | — | — |
| 15 | 0 | 0 | 0 | — | 3 | 2 | — | — | — | — | — | — | — | — | — | — | — | — | — | — |
| 16 | 1 | 0 | 0 | — | 3 | 3 | 2 | 0 | 3 | — | 3 | — | 1 | — | 0 | — | 1 | — | 0 | — |
| 17 | 0 | 0 | 3 | — | 2 | 0 | — | — | — | — | — | — | — | — | — | — | — | — | — | — |
| 18 | 0 | 0 | — | — | 1 | 3 | 0 | — | 0 | — | 3 | — | 2 | — | 0 | — | 0 | — | 3 | — |
| 19 | 1 | 0 | 0 | — | 0 | 0 | 1 | — | 0 | — | 0 | — | 1 | — | 3 | — | 0 | — | 1 | — |
| 20 | 1 | 0 | 0 | — | 0 | 0 | 1 | — | 0 | — | 2 | — | 0 | — | 1 | — | 0 | — | 0 | — |
| 21 | 2 | 0 | 1 | — | 0 | 0 | 0 | — | 0 | — | 0 | — | 0 | — | 2 | — | 0 | — | 3 | — |
| 22 | 0 | 0 | 0 | — | — | 1 | 0 | — | 0 | — | 3 | — | 0 | — | 2 | — | 1 | — | 1 | — |
| 23 | 0 | 0 | 0 | — | 0 | 0 | 0 | — | 2 | — | 1 | — | 1 | — | 2 | — | 1 | — | 0 | — |
| 24 | 0 | 0 | 1 | — | 0 | 0 | 1 | — | 0 | — | 1 | — | 0 | — | 2 | — | 0 | — | 0 | — |
| 25 | 0 | 0 | 0 | — | 3 | 2 | 3 | — | 1 | — | — | — | — | — | — | — | 0 | — | — | — |
| 26 | 0 | 0 | 0 | — | 3 | 3 | 1 | — | 2 | — | 2 | — | 0 | — | 0 | — | 2 | — | 3 | — |
| 27 | 0 | 0 | 0 | — | 3 | 2 | 3 | — | 3 | — | 3 | — | 2 | — | 1 | — | 1 | — | 0 | — |
| 28 | 0 | 0 | 1 | — | 3 | 3 | 3 | — | 3 | — | 3 | — | 3 | — | 2 | — | 3 | — | 1 | — |
| 29 | 2 | — | 1 | — | 1 | 0 | 0 | — | 2 | — | 0 | — | 1 | — | 0 | — | — | — | 1 | — |
| 30 | 1 | 0 | 1 | — | 0 | 0 | — | — | — | — | — | — | — | — | — | — | — | — | — | — |
| 33 | 0 | 0 | 1 | — | 3 | 3 | 0 | — | 0 | — | 1 | — | 0 | — | 2 | — | 0 | — | 0 | — |
| 34 | 0 | 0 | 1 | — | 0 | 3 | 1 | — | 0 | — | 0 | — | 0 | — | 0 | — | 0 | — | 1 | — |
| 35 | 0 | 0 | 0 | — | 0 | 2 | 0 | — | 1 | — | 0 | — | 1 | — | 1 | — | 0 | — | 1 | — |
| 36 | 0 | 0 | 1 | — | 0 | 1 | 1 | — | 0 | — | 0 | — | 0 | — | 0 | — | 0 | — | 1 | — |
| 37 | 0 | 0 | — | — | 3 | 3 | 0 | — | 2 | — | 0 | — | 0 | — | 0 | — | 0 | — | 0 | — |
| 38 | 0 | 0 | — | — | 3 | 3 | 2 | — | 3 | — | 3 | — | 1 | — | 0 | — | 0 | — | 2 | — |
| 39 | 0 | 0 | — | — | 3 | 3 | 0 | — | 1 | — | 3 | — | 1 | — | 0 | — | 0 | — | 3 | — |
| 40 | 0 | 0 | — | — | 3 | 3 | 2 | — | 1 | — | 3 | — | 2 | — | 0 | — | 0 | — | 3 | — |
| 41 | 0 | 0 | 1 | — | 3 | 3 | 3 | — | 2 | — | 3 | — | 2 | — | 0 | — | 0 | — | 1 | — |
| 44 | 0 | 0 | 0 | — | 3 | 3 | — | — | — | — | — | — | — | — | — | — | — | — | — | — |

The toxicity of a number of the pyrimidine derivatives of this invention towards a variety of insect pests was investigated and the tests conducted and results obtained are set out below. The compounds of the invention were in each case used in the form of a liquid preparation containing 0.1% by weight of the compound. The preparations were made by dissolving each of the compounds in a mixture of solvents consisting of 4 parts by volume of acetone and 1 part by volume of diacetone alcohol. The solutions were then diluted with water containing 0.01% by weight of a wetting agent sold under the trade name of LISSAPOL NX until the liquid preparations contained the required concentration of the compound LISSAPOL is a Trade Mark).

The test procedure adopted with regard to each test insect was basically the same and comprised supporting a number of the insects on some medium which may be a host plant or some foodstuff on which the insect feeds, and treating either or both the insect and the medium with the preparations. The mortality of the insects was then assessed at periods varying from one to three days after the treatment.

The results of the tests are given below in Table III. In this Table the first column indicates the compound used. Each of the subsequent columns indicates the name of the test insect, the host plant or medium on which it was supported, and the number of days which were allowed to elapse after treatment before assessing the percentage of insects which had been killed. The assessment is expressed in integers which range from 0 to 3.

0 represents less than 30% kill
1 represents from 30–49% kill
2 represents from 50–90% kill
3 represents over 90% kill The concentration of the invention compound in the solutions used was 1,000 parts per million for all the pests except in the cases of *Aedes aegypta* and *Meloidogyne incognita* when the concentration of the invention compound in the solution used was 100 parts per million.

TABLE III

| Compound No. | AEDES AEGYPTA | APHIS FABAE | MACROSIPHUM PISI | TETRANYCHUS TELARIUS | TETRANYCHUS TELARIUS | PHAEDON COCHLEARIAE | MELOIDOGYNE INCOGNITA |
|---|---|---|---|---|---|---|---|
| | Mosquito larva Water — | Black aphid Broad Bean 2 days | Green aphid Broad Bean 2 days | Red Spider mite French Bean 3 days | Red Spider egg French Bean 3 days | Mustard beetle Mustard paper 2 days | Root Knot nematode Water 2 days |
| 5 | 0 | 2 | 3 | 2 | 0 | — | — |
| 6 | 0 | 2 | 3 | 0 | 0 | — | — |
| 9 | 0 | 2 | 2 | 0 | 0 | — | — |
| 17 | 0 | 2 | 2 | 0 | 0 | — | — |
| 19 | 2 | 0 | 0 | 2 | 0 | — | — |
| 22 | 1 | 0 | 0 | 2 | 3 | 2 | — |
| 30 | 3 | 1 | 1 | 0 | 0 | — | — |
| 35 | — | — | 2 | 0 | 0 | — | 1 |
| 36 | 3 | — | — | — | — | — | 3 |
| 37 | — | — | — | — | — | — | 3 |
| 38 | 3 | — | — | — | — | — | — |
| 40 | 2 | — | — | — | — | — | — |
| 41 | 2 | — | — | — | — | — | — |
| 45 | 2 | — | — | — | — | — | — |

What we claim is:

1. A fungicidal composition comprising, as active ingredient, a fungicidally effective amount of a pyrimidine derivative selected from the group consisting of compounds having the formula:

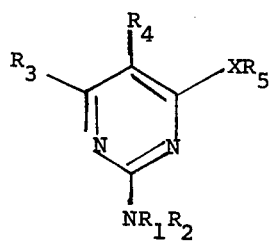

wherein $R_1$ and $R_2$ represent atoms of hydrogen, lower alkyl, halophenyl or together with the adjacent N-atom form a piperidino, morpholino or piperazino ring; $R_3$ and $R_4$ represent atoms of hydrogen, halogen, lower alkyl, phenyl, benzyl, lower alkenyl or nitro; X represents an atom of oxygen or sulphur; and $R_5$ is a carbonyl or sulphonyl group bearing directly, or through an oxygen or sulphur atom, a lower alkyl, lower alkenyl, phenyl or nitro-, halo, lower alkylphenyl radical; or furyl or piperidino and the acid-addition salts thereof and a major amount of a carrier for said active ingredient.

2. A composition according to claim 1 including a wetting agent.

3. A composition according to claim 1 wherein the active ingredient is one wherein $R_1$ and $R_2$ represent hydrogen atoms, lower alkyl radicals, a halophenyl radical, a piperidino radical, a morpholino radical or a 1-methyl piperazin-4-yl radical; $R_3$ represents a hydrogen atom, a lower alkyl radical or a phenyl radical; $R_4$ represents an atom of hydrogen or bromine, a lower alkyl, lower alkenyl, or benzyl radical, or a nitro group; X represents an atom of oxygen or sulphur; and $R_5$ is a carbonyl or sulphonyl group bearing directly, or through an atom of oxygen or sulphur, a lower alkyl radical, a lower alkenyl radical, a phenyl radical or a nitro-, halo-, lower alkylsubstituted phenyl radical, a piperidino radical, a furyl radical, or a styryl radical.

4. A composition according to claim 1 wherein the active ingredient is one wherein $R_1$ and $R_2$ are hydrogen or lower alkyl radicals; $R_3$ is a lower alkyl radical; $R_4$ is a lower alkyl radical having 2 to 6 carbon atoms; and $R_5$ is a carbonyl or sulphonyl group bearing a lower alkyl radical, a lower alkoxy radical, a phenyl radical or a styryl radical.

5. A composition according to claim 1 wherein the active ingredient is one wherein $R_1$ and $R_2$ are both methyl radicals or $R_1$ is hydrogen and $R_2$ is an ethyl radical; $R_3$ is a methyl radical; $R_4$ is butyl or amyl radical; X is an atom of oxygen; and $R_5$ is lower alkyl, lower alkoxy or phenyl radical.

6. A composition according to claim 1 wherein the active ingredient is 5-n-butyl-2-dimethylamino-4-methyl-6-phenyl-carbonyloxy-pyrimidine.

7. A method of combating undesired fungal infections in plants which comprises applying to the locus of the plant a fungicidally effective amount of a pyrimidine derivative selected from the group consisting of compounds having the formula:

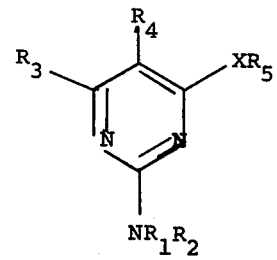

wherein $R_1$ and $R_2$ represent atoms of hydrogen, lower alkyl, halophenyl or together with the adjacent N-atom form a piperidino, morpholino or piperazino ring; $R_3$ and $R_4$ represent atoms of hydrogen, halogen, lower alkyl, phenyl, benzyl, lower alkenyl or nitro; X represents an atom of oxygen or sulphur; and $R_5$ is a carbonyl or sulphonyl group bearing directly, or through an oxygen or sulphur atom, a lower alkyl, lower alkenyl, phenyl or nitro-, halo-, lower alkyl-phenyl radical; or furyl or piperidino and the acid-addition salts thereof.

8. A method of combating insect infestations in plants which comprises applying to the locus of the plant an insecticidally effective amount of a pyrimidine derivative selected from the group consisting of compounds having the formula:

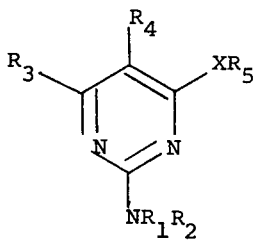

wherein $R_1$ and $R_2$ represent atoms of hydrogen, lower alkyl, halophenyl or together with the adjacent N-atom form a piperidino, morpholino or piperazino ring; $R_3$ and $R_4$ represent atoms of hydrogen, halogen, lower alkyl, phenyl, benzyl, lower alkenyl or nitro; X represents an atom of oxygen or sulphur; and $R_5$ is a carbonyl or sulphonyl group bearing directly, or through an oxygen or sulphur atom, a lower alkyl, lower alkenyl, phenyl or nitro-, halo-, lower alkyl-phenyl radical; or furyl or piperidino and the acid-addition salts thereof.

9. A method of combating plant insects and fungus which comprises applying to a plant or to seeds thereof an insecticidally and fungicidally effective amount of a composition as claimed in claim 1.

10. A method of treating agricultural soil to combat plant insects and fungus comprising applying to the soil an insecticidally and fungicidally effective amount of a composition as claimed in claim 1.

* * * * *

UNITED STATES PATENT OFFICE
CERTIFICATE OF CORRECTION

Patent No. 3,962,442      Dated June 8, 1976

Inventor(s) Brian Kenneth Snell and Ranajit Ghosh

It is certified that error appears in the above-identified patent and that said Letters Patent are hereby corrected as shown below:

<u>In the heading of the patent</u>, the first name of the inventor "Ghosh" should be corrected to read --Ranajit--

The foreign application priority data should be added as follows:

--[30]    Foreign Application Priority Data

March 31, 1966   Great Britain.....14270/66--

Signed and Sealed this

Fifth Day of October 1976

[SEAL]

Attest:

RUTH C. MASON
*Attesting Officer*

C. MARSHALL DANN
*Commissioner of Patents and Trademarks*